(12) United States Patent
Watanabe et al.

(10) Patent No.: US 11,899,002 B2
(45) Date of Patent: Feb. 13, 2024

(54) GAS SENSOR AND METHOD FOR CONTROLLING OPERATION OF GAS SENSOR

(71) Applicant: NGK INSULATORS, LTD., Nagoya (JP)

(72) Inventors: Yusuke Watanabe, Nagoya (JP); Takayuki Sekiya, Nisshin (JP)

(73) Assignee: NGK INSULATORS, LTD., Nagoya (JP)

(*) Notice: Subject to any disclaimer, the term of this patent is extended or adjusted under 35 U.S.C. 154(b) by 97 days.

(21) Appl. No.: 17/208,060

(22) Filed: Mar. 22, 2021

(65) Prior Publication Data

US 2021/0302400 A1 Sep. 30, 2021

(30) Foreign Application Priority Data

Mar. 25, 2020 (JP) ................................ 2020-054002

(51) Int. Cl.
| | |
|---|---|
| *G01N 33/00* | (2006.01) |
| *G01N 27/419* | (2006.01) |
| *G01N 27/41* | (2006.01) |
| *G01N 27/407* | (2006.01) |
| *G01N 27/409* | (2006.01) |

(52) U.S. Cl.
CPC ....... *G01N 33/0037* (2013.01); *G01N 27/409* (2013.01); *G01N 27/4073* (2013.01); *G01N 27/41* (2013.01); *G01N 27/419* (2013.01)

(58) Field of Classification Search
CPC .......... G01N 33/0037; G01N 27/4073; G01N 27/407; G01N 27/409; G01N 27/41
See application file for complete search history.

(56) References Cited

U.S. PATENT DOCUMENTS

| | | |
|---|---|---|
| 5,763,763 A | 6/1998 | Kato et al. |
| 2018/0094564 A1* | 4/2018 | Okamoto ........... G01N 27/4071 |

FOREIGN PATENT DOCUMENTS

| | | |
|---|---|---|
| JP | 3050781 B2 | 3/2000 |
| JP | 2014-190940 A | 10/2014 |
| JP | 2014-209128 A | 11/2014 |

* cited by examiner

*Primary Examiner* — Caitlyn Mingyun Sun
(74) *Attorney, Agent, or Firm* — MATTINGLY & MALUR, PC

(57) ABSTRACT

A limiting-current type gas sensor including a sensor element including a base part made of an oxygen-ion conductive solid electrolyte and measuring concentration of NOx in a measurement gas includes: a pump cell including a first electrode disposed to be capable of being in contact with a gas introduced into the element and a second electrode disposed so that a part made of the solid electrolyte is located between the first electrode and the second electrode; and a pumping diagnostic part to determine whether an inter-electrode electric field produced in the part made of the solid electrolyte through application of a predetermined pump voltage between the electrodes exceeds a first threshold, and, when the inter-electrode electric field exceeds the first threshold, the predetermined pump voltage is reduced so that the inter-electrode electric field falls below the first threshold.

20 Claims, 6 Drawing Sheets

GAS SENSOR AND METHOD FOR CONTROLLING OPERATION OF GAS SENSOR

CROSS-REFERENCE TO RELATED APPLICATION

The present application claims priority from Japanese application JP2020-054002, filed on Mar. 25, 2020, the contents of which is hereby incorporated by reference into this application.

BACKGROUND OF THE INVENTION

Field of the Invention

The present invention relates to a gas sensor for determining the concentration of nitrogen oxides (NOx), and, in particular, to control of operation thereof.

Description of the Background Art

A limiting-current type gas sensor (NOx sensor) including a sensor element containing an oxygen-ion conductive solid electrolyte (e.g., $ZrO_2$) as a main component has already been known (see, for example, Japanese Patent No. 3050781). In determining a NOx concentration using such a gas sensor, a measurement gas is first introduced into a space (an internal space) inside the sensor element under predetermined diffusion resistance, and oxygen in the measurement gas is pumped out by a two-stage electrochemical pump cell, for example, referred to as a main pump cell and an auxiliary pump cell (a first electrochemical pump cell and a second electrochemical pump cell in Japanese Patent No. 3050781) to sufficiently reduce an oxygen concentration of the measurement gas in advance. NOx in the measurement gas is then reduced or decomposed by a measurement electrode (third inner pump electrode in Japanese Patent No. 3050781) functioning as a reduction catalyst, and oxygen thus generated is pumped out by an electrochemical pump cell (a third electrochemical pump cell in Japanese Patent No. 3050781) different from the above-mentioned electrochemical pump cell, including the measurement electrode, and, for example, referred to as a measurement pump cell. The NOx concentration is determined using a constant functional relationship between a current (NOx current) flowing through the measurement pump cell and the NOx concentration.

In the gas sensor (NOx sensor), use of Pt to which Au has been added (an Au—Pt alloy) as a metal component of an inner pump electrode located in the internal space and forming the main pump cell in order to suppress decomposition of NOx caused when the main pump cell pumps out oxygen from the internal space and to enhance NOx detection accuracy has already been known (see, for example, Japanese Patent Application Laid-Open No. 2014-190940 and Japanese Patent Application Laid-Open No. 2014-209128).

A gas sensor as described above is typically used with a sensor element maintained at a predetermined temperature (element driving temperature) by a heater included in the sensor element to activate an oxygen-ion conductive solid electrolyte contained in the sensor element. When the gas sensor is in use (in steady-state operation to measure the concentration), a voltage of approximately several hundred millivolts is applied between a pair of pump electrodes of each pump cell for pumping (pumping out or pumping in) of oxygen under control performed by a controller included in the gas sensor.

When use of such a gas sensor is started (at the start of the gas sensor), a sensor element is heated from a low temperature (e.g., room temperature) to a raised temperature, and, further, a pump cell pumps out oxygen to remove oxygen in air having entered an internal space while the gas sensor is not in use. A voltage applied between a pair of pump electrodes at the time has a value of several volts greater than that in the steady-state operation for the purpose of minimizing time until the gas sensor becomes operational. Not only at the start, such a large voltage is also applied between the pump electrodes at any timing when the concentration is not measured.

An excessive increase in voltage applied between the pair of pump electrodes of each pump cell has caused a problem of cracking of a solid electrolyte located between the pump electrodes. This is presumably because oxygen in the solid electrolyte located between the pump electrodes moves due to a strong electric field produced between the pump electrodes by application of a pump voltage, to form a region of less oxygen content in the solid electrolyte to thereby reduce the strength. Once such cracking occurs in the sensor element, the gas sensor can no longer properly measure a gas concentration. For this reason, the voltage applied between the pair of pump electrodes of each pump cell is required to be properly controlled even not in the steady-state operation.

SUMMARY

The present invention relates to a gas sensor for determining the concentration of nitrogen oxides (NOx), and is, in particular, directed to how to control operation thereof.

According to the present invention, a limiting-current type gas sensor measuring concentration of NOx in a measurement gas includes: a sensor element including: a base part made of an oxygen-ion conductive solid electrolyte; at least one pump cell as an electrochemical pump cell including: a first electrode disposed to be capable of being in contact with a gas introduced into the sensor element; and a second electrode disposed so that a part made of the solid electrolyte is located between the first electrode and the second electrode, and capable of externally pumping out oxygen from a region that the first electrode faces through application of a predetermined pump voltage between the first electrode and the second electrode; and a heater part buried in the sensor element and heating the sensor element; and a controller controlling operation of the gas sensor, the controller including a pumping diagnostic part configured to make a first diagnosis to determine whether an inter-electrode electric field exceeds a first threshold, the inter-electrode electric field being produced in the part made of the solid electrolyte between the first electrode and the second electrode through application of the predetermined pump voltage between the first electrode and the second electrode, wherein when the inter-electrode electric field exceeds the first threshold, the controller reduces the predetermined pump voltage so that the inter-electrode electric field falls below the first threshold.

According to the gas sensor, a pumping diagnosis is made to suitably suppress movement, within the pump cell, of oxygen contained in the solid electrolyte located between the first electrode and the second electrode constituting the pump cell for reducing oxygen contained in the solid electrolyte.

The pumping diagnostic part is preferably configured to further make a second diagnosis to determine whether a temperature index value exceeds a second threshold, the temperature index value having a positive correlation with temperature in the part made of the solid electrolyte between the first electrode and the second electrode, and the pumping diagnostic part makes the first diagnosis when the temperature index value is equal to or greater than the second threshold.

In this case, the pumping diagnosis can be made in view of properties of the solid electrolyte in that the solid electrolyte at a low temperature is less likely to cause reduction in oxygen.

The concentration of NOx in the measurement gas is more preferably measured in a steady state of operation, the steady state of operation being a state in which the sensor element is maintained at a predetermined element driving temperature by being heated by the heater part, and oxygen partial pressure in the region that the first electrode faces in the at least one pump cell is maintained at or below a predetermined value, the at least one pump cell performs preparatory pumping to pump out oxygen from the region while the heater part raises temperature of the sensor element to the element driving temperature, so that the gas sensor transitions from a non-steady state of operation to the steady state of operation, and the pumping diagnostic part makes the first diagnosis and the second diagnosis during transition from the non-steady state of operation to the steady state of operation.

In this case, cracking caused by reduction in oxygen from the solid electrolyte located between the first electrode and the second electrode is suitably suppressed even in a case where a large pump voltage is applied with a temperature rise performed by the heater part to cause the gas sensor to early transition from the non-steady state of operation to the steady state of operation in which the concentration of NOx can be measured. Light-off time can thereby be reduced without reducing the strength of the sensor element. This manner also contributes to extension of the lifetime of the sensor element.

It is thus an object of the present invention to achieve a gas sensor in which a voltage applied between a pair of pump electrodes constituting a pump cell of a sensor element is suitably controlled.

These and other objects, features, aspects and advantages of the present invention will become more apparent from the following detailed description of the present invention when taken in conjunction with the accompanying drawings.

DESCRIPTION OF THE PREFERRED EMBODIMENTS

<General Configuration of Gas Sensor>

A general configuration of a gas sensor 100 including a sensor element 101 according to the present embodiment will be described first. In the present embodiment, the gas sensor 100 is a limiting-current type NOx sensor sensing NOx and measuring the concentration thereof using the sensor element 101. The gas sensor 100 further includes a controller 110 controlling operation of each part and identifying the NOx concentration based on a NOx current flowing through the sensor element 101.

Figure 1:
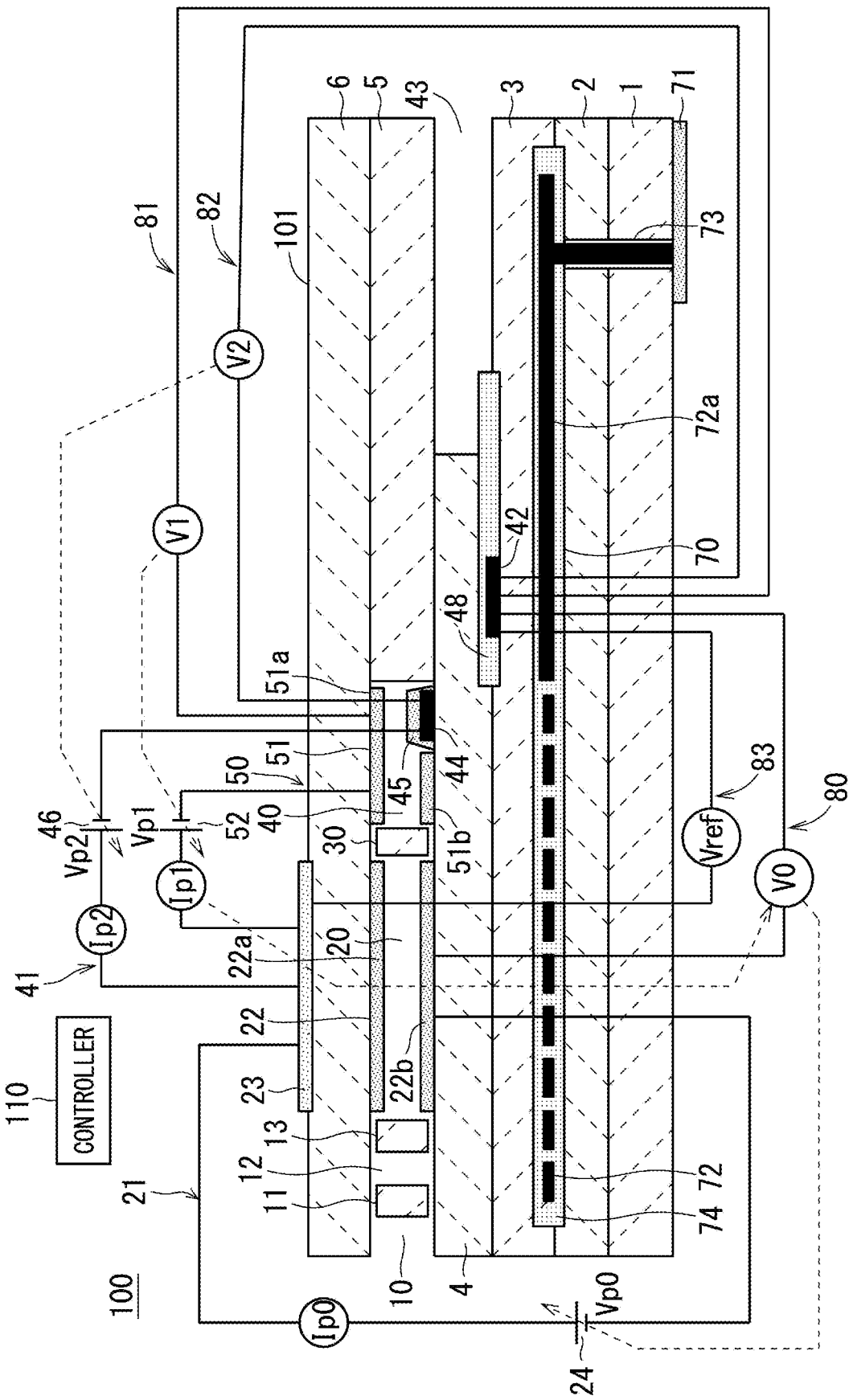
FIG. 1 is a diagram schematically showing one example of a configuration of a gas sensor 100, including a vertical cross-sectional view taken along a longitudinal direction of a sensor element 101.

FIG. 1 is a diagram schematically showing one example of a configuration of the gas sensor 100, including a vertical cross-sectional view taken along a longitudinal direction of the sensor element 101.

The sensor element 101 is a planar (elongated planar) element having a structure in which six solid electrolyte layers, namely, a first substrate layer 1, a second substrate layer 2, a third substrate layer 3, a first solid electrolyte layer 4, a spacer layer 5, and a second solid electrolyte layer 6 each made of zirconia ($ZrO_2$) (e.g., yttria stabilized zirconia (YSZ)) as an oxygen-ion conductive solid electrolyte are laminated in the stated order from a bottom side of FIG. 1. The solid electrolyte forming these six layers is dense and airtight. A surface on an upper side and a surface on a lower side of each of these six layers in FIG. 1 are hereinafter also simply referred to as an upper surface and a lower surface, respectively. A part of the sensor element 101 made of the solid electrolyte as a whole is generically referred to as a base part.

The sensor element 101 is manufactured, for example, by performing predetermined processing, printing of circuit patterns, and the like on ceramic green sheets corresponding to the respective layers, then laminating them, and further firing them for integration.

Between a lower surface of the second solid electrolyte layer 6 and an upper surface of the first solid electrolyte layer 4 in one leading end portion of the sensor element 101, a gas inlet 10, a first diffusion control part 11, a buffer space 12, a second diffusion control part 13, a first internal space 20, a third diffusion control part 30, and a second internal space 40 are formed adjacent to each other to communicate in the stated order.

The gas inlet 10, the buffer space 12, the first internal space 20, and the second internal space 40 are spaces (regions) inside the sensor element 101 looking as if they were provided by hollowing out the spacer layer 5, and having an upper portion, a lower portion, and a side portion respectively defined by the lower surface of the second solid electrolyte layer 6, the upper surface of the first solid electrolyte layer 4, and a side surface of the spacer layer 5.

The first diffusion control part 11, the second diffusion control part 13, and the third diffusion control part 30 are each provided as two horizontally long slits (whose openings have longitudinal directions perpendicular to the page of FIG. 1). A part extending from the gas inlet 10 to the second internal space 40 is also referred to as a gas distribution part.

At a location farther from the leading end than the gas distribution part is, a reference gas introduction space 43 having a side portion defined by a side surface of the first solid electrolyte layer 4 is provided between an upper surface of the third substrate layer 3 and a lower surface of the spacer layer 5. For example, air is introduced into the reference gas introduction space 43 as a reference gas when the NOx concentration is measured.

An air introduction layer 48 is a layer made of porous alumina, and the reference gas is introduced into the air introduction layer 48 through the reference gas introduction space 43. The air introduction layer 48 is formed to cover a reference electrode 42.

The reference electrode 42 is an electrode formed to be sandwiched between the upper surface of the third substrate layer 3 and the first solid electrolyte layer 4, and the air introduction layer 48 leading to the reference gas introduction space 43 is provided around the reference electrode 42 as described above. As will be described below, an oxygen concentration (oxygen partial pressure) in the first internal space 20 and the second internal space 40 can be measured using the reference electrode 42.

In the gas distribution part, the gas inlet 10 is a part opening to an external space, and a measurement gas is taken from the external space into the sensor element 101 through the gas inlet 10.

The first diffusion control part 11 is a part providing predetermined diffusion resistance to the measurement gas taken through the gas inlet 10.

The buffer space 12 is a space provided to guide the measurement gas introduced through the first diffusion control part 11 to the second diffusion control part 13.

The second diffusion control part 13 is a part providing predetermined diffusion resistance to the measurement gas introduced from the buffer space 12 into the first internal space 20.

In introducing the measurement gas from outside the sensor element 101 into the first internal space 20, the measurement gas having abruptly been taken into the sensor element 101 through the gas inlet 10 due to pressure fluctuations (pulsation of exhaust pressure in a case where the measurement gas is an exhaust gas of a vehicle) of the measurement gas in the external space is not directly introduced into the first internal space 20 but is introduced into the first internal space 20 after concentration fluctuations of the measurement gas are canceled through the first diffusion control part 11, the buffer space 12, and the second diffusion control part 13. This makes the concentration fluctuations of the measurement gas introduced into the first internal space 20 almost negligible.

The first internal space 20 is provided as a space to adjust oxygen partial pressure of the measurement gas introduced through the second diffusion control part 13. The oxygen partial pressure is adjusted by operating a main pump cell 21.

The main pump cell 21 is an electrochemical pump cell including an inner pump electrode 22, an outer (out-of-space) pump electrode 23, and the second solid electrolyte layer 6 sandwiched between these electrodes. The inner pump electrode 22 has a ceiling electrode portion 22a provided on substantially the entire lower surface of a portion of the second solid electrolyte layer 6 facing the first internal space 20, and the outer pump electrode 23 is provided in a region, on an upper surface of the second solid electrolyte layer 6 (one main surface of the sensor element 101), corresponding to the ceiling electrode portion 22a to be exposed to the external space.

The inner pump electrode 22 is formed on upper and lower solid electrolyte layers (the second solid electrolyte layer 6 and the first solid electrolyte layer 4) defining the first internal space 20. Specifically, the ceiling electrode portion 22a is formed on the lower surface of the second solid electrolyte layer 6, which provides a ceiling surface to the first internal space 20, and a bottom electrode portion 22b is formed on the upper surface of the first solid electrolyte layer 4, which provides a bottom surface to the first internal space 20. The ceiling electrode portion 22a and the bottom electrode portion 22b are connected by a conducting portion (not illustrated) provided on a side wall surface (an inner surface) of the spacer layer 5 forming opposite side wall portions of the first internal space 20.

The ceiling electrode portion 22a and the bottom electrode portion 22b are provided to be rectangular in plan view. Only the ceiling electrode portion 22a or only the bottom electrode portion 22b may be provided. The ceiling electrode portion 22a and the bottom electrode portion 22b each have a planar size of 5.0 mm$^2$ to 15.0 mm$^2$.

The inner pump electrode 22 and the outer pump electrode 23 are each formed as a porous cermet electrode. In particular, the inner pump electrode 22 to be in contact with the measurement gas is formed using a material having a weakened reducing ability with respect to a NOx component in the measurement gas. For example, the inner pump electrode 22 is formed, for example, as a cermet electrode of an Au—Pt alloy containing Au of approximately 0.6 wt % to 1.4 wt % and $ZrO_2$ to have a porosity of 5% to 40% and a thickness of 5 μm to 20 μm. A weight ratio Pt:$ZrO_2$ of the Au—Pt alloy and $ZrO_2$ is only required to be approximately 7.0:3.0 to 5.0:5.0.

On the other hand, the outer pump electrode 23 is formed, for example, as a cermet electrode of Pt or an alloy thereof and $ZrO_2$ to be rectangular in plan view. The outer pump electrode 23 has a planar size of 5.0 mm$^2$ to 15.0 mm$^2$.

The main pump cell 21 can pump out oxygen in the first internal space 20 to the external space or pump in oxygen in the external space to the first internal space 20 by applying, from a variable power supply 24, a desired pump voltage Vp0 between the inner pump electrode 22 and the outer pump electrode 23 to allow a main pump current Ip0 to flow between the inner pump electrode 22 and the outer pump electrode 23 in a positive or negative direction. The pump voltage Vp0 applied between the inner pump electrode 22 and the outer pump electrode 23 in the main pump cell 21 is also referred to as a main pump voltage Vp0.

To detect the oxygen concentration (oxygen partial pressure) in an atmosphere in the first internal space 20, the inner pump electrode 22, the second solid electrolyte layer 6, the spacer layer 5, the first solid electrolyte layer 4, the third substrate layer 3, and the reference electrode 42 constitute a main sensor cell 80 as an electrochemical sensor cell.

The oxygen concentration (oxygen partial pressure) in the first internal space 20 can be known by measuring electromotive force V0 in the main sensor cell 80.

Furthermore, the controller 110 performs feedback control of the main pump voltage Vp0 so that the electromotive force V0 is constant, thereby to control the main pump current Ip0. The oxygen concentration in the first internal space 20 is thereby maintained at a predetermined constant value.

The third diffusion control part 30 is a part providing predetermined diffusion resistance to the measurement gas having an oxygen concentration (oxygen partial pressure) controlled by operation of the main pump cell 21 in the first internal space 20, and guiding the measurement gas to the second internal space 40.

The second internal space 40 is provided as a space to perform processing concerning measurement of the nitrogen oxide (NOx) concentration of the measurement gas introduced through the third diffusion control part 30. The NOx concentration is measured, mainly in the second internal space 40 in which the oxygen concentration has been adjusted by an auxiliary pump cell 50, further by operation of a measurement pump cell 41.

After the oxygen concentration (oxygen partial pressure) is adjusted in advance in the first internal space 20, the auxiliary pump cell 50 further adjusts the oxygen partial pressure of the measurement gas introduced through the third diffusion control part 30 in the second internal space 40. The oxygen concentration in the second internal space 40 can thereby be maintained constant with high accuracy, and thus the NOx concentration can be measured with high accuracy in the gas sensor 100.

The auxiliary pump cell 50 is an auxiliary electrochemical pump cell including an auxiliary pump electrode 51, the outer pump electrode 23 (not limited to the outer pump electrode 23 and only required to be any appropriate electrode outside the sensor element 101), and the second solid electrolyte layer 6. The auxiliary pump electrode 51 has a ceiling electrode portion 51a provided on substantially the entire lower surface of a portion of the second solid electrolyte layer 6 facing the second internal space 40.

The auxiliary pump electrode 51 is provided in the second internal space 40 in a similar form to the inner pump electrode 22 provided in the first internal space 20 described previously. That is to say, the ceiling electrode portion 51a is formed on the second solid electrolyte layer 6, which provides a ceiling surface to the second internal space 40, and a bottom electrode portion 51b is formed on the first solid electrolyte layer 4, which provides a bottom surface to the second internal space 40. The ceiling electrode portion 51a and the bottom electrode portion 51b are rectangular in plan view, and are connected by a conducting portion (not illustrated) provided on the side wall surface (inner surface) of the spacer layer 5 forming opposite side wall portions of the second internal space 40. The ceiling electrode portion 51a has a planar size of 2.0 mm$^2$ to 6.0 mm$^2$, and the bottom electrode portion 51b has a planar size of 1.0 mm$^2$ to 4.0 mm$^2$.

As with the inner pump electrode 22, the auxiliary pump electrode 51 is formed using a material having a weakened reducing ability with respect to the NOx component in the measurement gas.

The auxiliary pump cell 50 can pump out oxygen in an atmosphere in the second internal space 40 to the external space or pump in oxygen in the external space to the second internal space 40 by applying a desired voltage (an auxiliary pump voltage) Vp1 between the auxiliary pump electrode 51 and the outer pump electrode 23 under control performed by the controller 110.

To control the oxygen partial pressure in the atmosphere in the second internal space 40, the auxiliary pump electrode 51, the reference electrode 42, the second solid electrolyte layer 6, the spacer layer 5, the first solid electrolyte layer 4, and the third substrate layer 3 constitute an auxiliary sensor cell 81 as an electrochemical sensor cell.

The auxiliary pump cell 50 performs pumping using a variable power supply 52 whose voltage is controlled based on electromotive force V1 detected in the auxiliary sensor cell 81 in accordance with the oxygen partial pressure in the second internal space 40. The oxygen partial pressure in the atmosphere in the second internal space 40 is thereby controlled to a low partial pressure having substantially no effect on measurement of NOx.

At the same time, a resulting auxiliary pump current Ip1 is used to control the electromotive force in the main sensor cell 80. Specifically, the auxiliary pump current Ip1 is input, as a control signal, into the main sensor cell 80, and, through control of the electromotive force V0 therein, the oxygen partial pressure of the measurement gas introduced through the third diffusion control part 30 into the second internal space 40 is controlled to have a gradient that is always constant. In use as the NOx sensor, the oxygen concentration in the second internal space 40 is maintained at a constant value of approximately 0.001 ppm by the action of the main pump cell 21 and the auxiliary pump cell 50.

The measurement pump cell 41 measures the NOx concentration of the measurement gas in the second internal space 40. The measurement pump cell 41 is an electrochemical pump cell including a measurement electrode 44, the outer pump electrode 23, the second solid electrolyte layer 6, the spacer layer 5, and the first solid electrolyte layer 4. The measurement electrode 44 is provided on an upper surface of a portion of the first solid electrolyte layer 4 facing the second internal space 40 to be separated from the third diffusion control part 30.

The measurement electrode 44 is a porous cermet electrode. The measurement electrode 44 is formed, for example, as a cermet electrode of Pt or an alloy thereof and $ZrO_2$. The measurement electrode 44 also functions as a NOx reduction catalyst to reduce NOx existing in the atmosphere in the second internal space 40. Furthermore, the measurement electrode 44 is covered with a fourth diffusion control part 45. The measurement electrode 44 has a planar size of 0.2 mm$^2$ to 0.8 mm$^2$.

The fourth diffusion control part 45 is a film formed of a porous body containing alumina ($Al_2O_3$) as a main component. The fourth diffusion control part 45 plays a role in limiting the amount of NOx flowing into the measurement electrode 44, and also functions as a protective film of the measurement electrode 44.

The measurement pump cell 41 can pump out oxygen generated through decomposition of NOx in an atmosphere around the measurement electrode 44, and detect the amount of generated oxygen as a pump current Ip2 under control performed by the controller 110.

To detect the oxygen partial pressure around the measurement electrode 44, the second solid electrolyte layer 6, the spacer layer 5, the first solid electrolyte layer 4, the third substrate layer 3, the measurement electrode 44, and the reference electrode 42 constitute a measurement sensor cell 82 as an electrochemical sensor cell. A variable power supply 46 is controlled based on electromotive force V2 detected in the measurement sensor cell 82 in accordance with the oxygen partial pressure around the measurement electrode 44.

The measurement gas introduced into the second internal space 40 is to reach the measurement electrode 44 through the fourth diffusion control part 45 under a condition in which the oxygen partial pressure is controlled. NOx in the measurement gas around the measurement electrode 44 is reduced ($2NO \rightarrow N_2+O_2$) to generate oxygen. Oxygen as generated is to be pumped by the measurement pump cell 41, and, at this time, a voltage (measurement pump voltage) Vp2 of the variable power supply 46 is controlled so that the electromotive force V2 detected in the measurement sensor cell 82 is constant. The amount of oxygen generated around the measurement electrode 44 is proportional to the NOx concentration of the measurement gas, and thus the NOx concentration of the measurement gas is to be calculated using the pump current Ip2 in the measurement pump cell 41. The pump current Ip2 is hereinafter also referred to as a NOx current Ip2.

If the measurement electrode 44, the first solid electrolyte layer 4, the third substrate layer 3, and the reference electrode 42 are combined to constitute an oxygen partial pressure detection means as an electrochemical sensor cell, electromotive force in accordance with a difference between the amount of oxygen generated through reduction of a NOx component in the atmosphere around the measurement electrode 44 and the amount of oxygen contained in reference air can be detected, and the concentration of the NOx component in the measurement gas can thereby be determined.

The second solid electrolyte layer 6, the spacer layer 5, the first solid electrolyte layer 4, the third substrate layer 3, the outer pump electrode 23, and the reference electrode 42 constitute an electrochemical sensor cell 83, and oxygen partial pressure of the measurement gas outside the sensor can be detected using electromotive force Vref obtained by the sensor cell 83.

The sensor element 101 further includes a heater part 70 playing a role in temperature adjustment of heating the sensor element 101 and maintaining the temperature thereof to enhance oxygen ion conductivity of the solid electrolyte forming the base part.

The heater part 70 mainly includes a heater electrode 71, a heater element 72, a heater lead 72a, a through hole 73, a heater insulating layer 74, and a heater resistance detection lead 75 (FIG. 2), which is not illustrated in FIG. 1. A portion of the heater part 70 other than the heater electrode 71 is buried in the base part of the sensor element 101.

The heater electrode 71 is an electrode formed to be in contact with a lower surface of the first substrate layer 1 (the other main surface of the sensor element 101).

The heater element 72 is a resistive heating element provided between the second substrate layer 2 and the third substrate layer 3. The heater element 72 generates heat by being powered from a heater power supply 76 (FIG. 2), which is not illustrated in FIG. 1, outside the sensor element 101 through the heater electrode 71, the through hole 73, and the heater lead 72a, which constitute a current-carrying path. The heater element 72 is made of Pt, or contains Pt as a main component. The heater element 72 is buried, in a predetermined range of the sensor element 101 in which the gas distribution part is provided, to oppose the gas distribution part in the thickness direction of the element. The heater element 72 is provided to have a thickness of approximately 10 μm to 20 μm.

In the sensor element 101, each part of the sensor element 101 can be heated to a predetermined temperature and the temperature can be maintained by allowing a current to flow through the heater electrode 71 to the heater element 72 to thereby cause the heater element 72 to generate heat. Specifically, the sensor element 101 is heated so that the temperature of the solid electrolyte and the electrodes in the vicinity of the gas distribution part is approximately 700° C. to 900° C. The oxygen ion conductivity of the solid electrolyte forming the base part in the sensor element 101 is enhanced by the heating. A heating temperature of the heater element 72 when the gas sensor 100 is in use (when the sensor element 101 is driven) is referred to as a sensor element driving temperature.

A degree of heat generation of the heater element 72 (heater temperature) is grasped by the magnitude of a resistance value (heater resistance) of the heater element 72. The heater resistance detection lead 75 is provided to measure the heater resistance.

<Controller>

Figure 2:
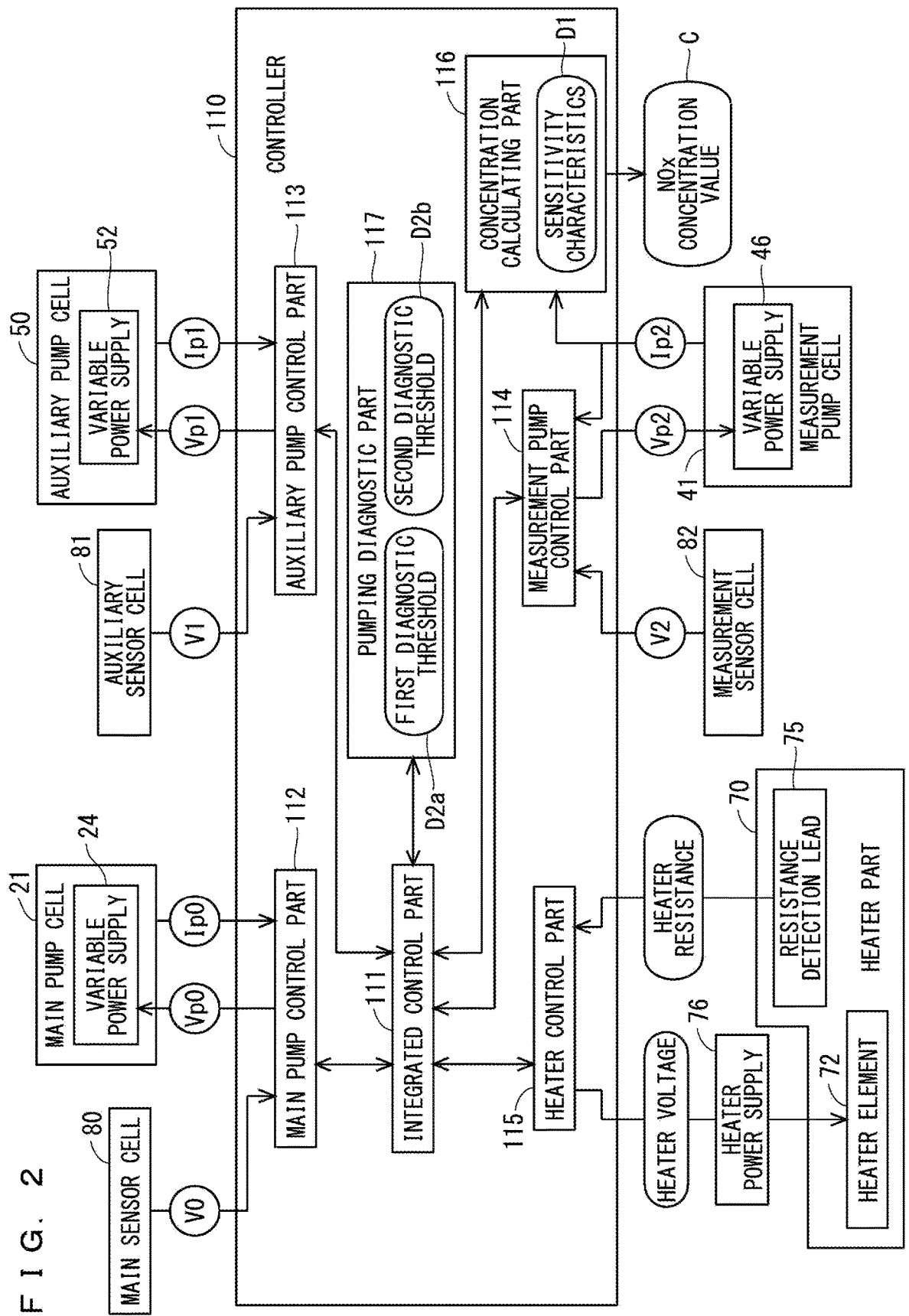
FIG. 2 is a diagram showing a functional configuration of a controller 110.

Functions of the controller 110 will be described in more detail next. FIG. 2 is a diagram showing a functional configuration of the controller 110 of the gas sensor 100.

The controller 110 is implemented by a general-purpose or dedicated computer, and includes, as functional components achieved by a CPU, memory, and the like thereof, an integrated control part 111, a main pump control part 112, an auxiliary pump control part 113, a measurement pump control part 114, a heater control part 115, a concentration calculating part 116, and a pumping diagnostic part 117. In a case where NOx contained in exhaust gas from an engine of a vehicle is a target of sensing and measurement of the gas sensor 100, and the sensor element 101 is installed onto an exhaust path, some or all the functions of the controller 110 may be implemented by an electronic control unit (ECU) mounted on the vehicle.

The integrated control part 111 integrally controls various types of processing performed in the controller 110. That is to say, the integrated control part 111 integrally controls operation for control performed by each of the above-mentioned control parts of the controller 110 on each of the pump cells, the heater, and the like for sensing of NOx, calculating the concentration, and the like, and controls calculating processing performed by the concentration calculating part 116 and diagnostic processing performed by the pumping diagnostic part 117.

The main pump control part 112 controls operation of the main pump cell 21, such as pumping out of oxygen from the first internal space 20 or pumping in of oxygen to the first internal space 20. In particular, in a steady state of operation, which will be described below, the main pump control part 112 acquires a value of the electromotive force V0 generated in the main sensor cell 80 in accordance with the oxygen partial pressure in the first internal space 20, performs feedback control of the main pump voltage Vp0 to be applied from the variable power supply 24 to the main pump cell 21 so that the value of the electromotive force V0 is in accordance with desired oxygen partial pressure, and acquires a value of the main pump current Ip0 flowing through the main pump cell 21 at that time.

The auxiliary pump control part 113 controls operation of the auxiliary pump cell 50, such as pumping out of oxygen from the second internal space 40. In particular, in the steady state of operation, which will be described below, the auxiliary pump control part 113 acquires a value of the electromotive force V1 generated in the auxiliary sensor cell 81 in accordance with the oxygen partial pressure in the second internal space 40, performs feedback control of the auxiliary pump voltage Vp1 to be applied from the variable power supply 52 to the auxiliary pump cell 50 so that the value of the electromotive force V1 is in accordance with desired oxygen partial pressure, and acquires a value of the auxiliary pump current Ip1 flowing through the auxiliary pump cell 50 at that time.

The measurement pump control part 114 controls operation of the measurement pump cell 41, such as pumping out of oxygen from a region near the measurement electrode 44. In particular, in the steady state of operation, which will be described below, the measurement pump control part 114 acquires a value of the electromotive force V2 generated in the measurement sensor cell 82 in accordance with the oxygen partial pressure near the measurement electrode 44, performs feedback control of the measurement pump voltage Vp2 to be applied from the variable power supply 46 to the measurement pump cell 41 so that the value of the electromotive force V2 is in accordance with desired oxygen partial pressure, and acquires a value of the pump current (NOx current) Ip2 flowing through the measurement pump cell 41 at that time.

The heater control part 115 controls operation of the heater part 70. Specifically, the heater control part 115 controls a heater voltage to be applied to the heater power supply 76 so that a value of the heater resistance (resistance of the heater element 72) obtained as a resistance value between the heater resistance detection lead 75 and the heater lead 72a is in accordance with a desired heating temperature. The heater element 72 generates heat so that the amount of heat generation is in accordance with the heater resistance controlled in this manner. The heater control part 115 controls the value of the heater resistance in accordance with the desired sensor element driving temperature, so that the sensor element driving temperature is achieved.

The concentration calculating part 116 acquires the value of the pump current (NOx current) Ip2 flowing through the measurement pump cell 41, calculates the NOx concentration based on sensitivity characteristics data D1 in which sensitivity characteristics set in advance for the sensor element 101 are described, and outputs the calculated NOx concentration.

In the gas sensor 100, oxygen contained in the measurement gas is pumped out by the main pump cell 21 and further the auxiliary pump cell 50 operated by the main pump control part 112 and the auxiliary pump control part 113, and the measurement gas having oxygen partial pressure sufficiently reduced to a degree (e.g., 0.0001 ppm to 1 ppm) having substantially no effect on measurement of NOx reaches the measurement electrode 44. NOx in the measurement gas having reached the measurement electrode 44 is reduced to generate oxygen. Oxygen as generated is pumped out by the measurement pump cell 41 under control performed by the measurement pump control part 114. A constant functional relationship between the NOx current Ip2 flowing at the pumping out and the concentration of NOx in the measurement gas is referred to as sensitivity characteristics.

The sensitivity characteristics are identified in advance using a plurality of types of model gases having known NOx concentrations prior to actual use of the gas sensor 100, and data thereof is stored as the sensitivity characteristics data D1 in the controller 110 (more particularly, in memory functioning as the concentration calculating part 116).

In actual use of the gas sensor 100, a signal representing the value of the NOx current Ip2 flowing in accordance with the NOx concentration of the measurement gas is momentarily provided to the concentration calculating part 116, and the concentration calculating part 116 successively calculates NOx concentrations based on the value and the identified sensitivity characteristics, and outputs values thereof (NOx concentration values) to the outside the controller 110. The NOx concentration of the measurement gas can thereby be known in almost real time using the gas sensor 100.

In the present embodiment, operation performed by each pump cell of the gas sensor 100 to output the NOx concentration and control thereof as described above, such as heating performed by the heater part 70 to maintain the sensor element 101 at the element driving temperature, pumping of oxygen from the measurement gas, pumping of oxygen generated by decomposition of NOx in the measurement gas, feedback control based on the electromotive force generated in the sensor cell to achieve the foregoing, and further calculating processing to output the NOx concentration based on the value of the NOx current Ip2, are referred to as "steady-state operation" to measure the NOx concentration in the gas sensor 100.

The pumping diagnostic part 117 makes a pumping diagnosis to diagnose a pumping condition of each of the main pump cell 21, the auxiliary pump cell 50, and the measurement pump cell 41 of the sensor element 101. Generally speaking, in the pumping diagnosis, whether the magnitude of an electric field produced between a pair of electrodes of each pump cell when the pump voltage is applied between the pair of electrodes for pumping operation exceeds a predetermined threshold (first diagnostic threshold) set in advance is determined. The result of the diagnosis is provided to the integrated control part 111, and the integrated control part 111 provides, as a result of the pumping diagnosis, control instructions for reducing the pump voltage for the pump cell in which it is determined that the magnitude of the electric field exceeds the first diagnostic threshold. An individual first diagnostic threshold may be set for each pump cell.

The electric field produced between the electrodes is reduced by the reduction of the pump voltage. This suitably suppresses movement, within the pump cell, of oxygen contained in the solid electrolyte located between the electrodes, which is caused as a result of production of an excessively large electric field having a magnitude equal to or greater than the first diagnostic threshold between the electrodes, for reducing oxygen contained in the solid electrolyte.

In the present embodiment, the magnitude of the electric field (inter-electrode electric field) produced in each pump cell through application of the pump voltage between the electrodes is calculated to be simplified as described below for ease of evaluation. Strictly speaking, each calculated value thus does not necessarily represent the magnitude of the electric field produced between the electrodes of each pump cell, and is nothing more than a relative evaluation value (an electric field evaluation value) indicating a relative magnitude of the electric field. At least in preparatory pumping processing, however, use of the calculated value as the value indicating the magnitude of the electric field does not cause any problems as it is unnecessary to compare the magnitude of the electric field between different pump cells.

First, as for the main pump cell 21, a value obtained by dividing a value of the main pump voltage Vp0 by the thickness of the second solid electrolyte layer 6 located between the ceiling electrode portion 22a of the inner pump electrode 22 and the outer pump electrode 23 is set to the magnitude of the electric field produced between the inner pump electrode 22 and the outer pump electrode 23.

As for the auxiliary pump cell 50, a value obtained by dividing a value of the auxiliary pump voltage Vp1 by the thickness of the second solid electrolyte layer 6 located between the ceiling electrode portion 51a of the auxiliary pump electrode 51 and the outer pump electrode 23 is similarly set to the magnitude of the electric field produced between the auxiliary pump electrode 51 and the outer pump electrode 23.

On the other hand, as for the measurement pump cell 41, a value obtained by dividing a value of the measurement pump voltage Vp2 by the sum of the thickness of the spacer layer 5 and the thickness of the second solid electrolyte layer 6 both being the solid electrolyte layers is set to the magnitude of the electric field produced between the measurement electrode 44 and the outer pump electrode 23.

The thickness of the spacer layer 5 and the thickness of the second solid electrolyte layer 6 are (known) values that can be identified in advance in the sensor element 101, and thus, in a case where they are identified, the pumping diagnosis based on the first diagnostic threshold can practically be made only by grasping the pump voltage in each pump cell. The thickness of the spacer layer 5 and the thickness of the second solid electrolyte layer 6 are each approximately 50 μm to 400 μm, for example. The spacer layer 5 and the second solid electrolyte layer 6 are not required to have the same thickness.

The pumping diagnosis may actually be made only when an index value (a temperature index value) having a positive correlation with the temperature of the solid electrolyte located between the pair of pump electrodes is equal to or greater than a predetermined threshold (second diagnostic threshold) set in advance, in view of the fact that oxygen contained in the solid electrolyte is significantly reduced when the temperature of the solid electrolyte forming the sensor element is high. This is in view of properties of the solid electrolyte in that the solid electrolyte located between the pair of pump electrodes is less likely to cause reduction in oxygen at a low temperature. The first diagnostic threshold is set so that oxygen is not significantly reduced from the solid electrolyte located between the pair of pump electrodes as long as the magnitude of the inter-electrode electric field is equal to or smaller than the first diagnostic threshold even if the solid electrolyte is in a state of being heated to a temperature equal to or greater than a temperature corresponding to the second diagnostic threshold. An individual second diagnostic threshold may be set for each pump cell.

Not the temperature of the solid electrolyte located between the pair of pump electrodes itself but the temperature index value is used because it is difficult to directly measure the temperature of the solid electrolyte located between the pair of pump electrodes.

The temperature index value to be the second diagnostic threshold is preferably set so that the temperature corresponding thereto is lower than the element driving temperature, but may be set so that the temperature corresponding thereto is equal to the element driving temperature.

To make the pumping diagnosis as described above, first diagnostic threshold data D2a in which the first diagnostic threshold is described and second diagnostic threshold data D2b in which the second diagnostic threshold is described are stored in advance in the controller 110 (more particularly, in memory functioning as the pumping diagnostic part 117).

The pumping diagnosis may continuously be made after the start of the gas sensor 100 even during the steady-state operation, but the most significant effect of the pumping diagnosis is obtained, and thus processing is effective when the preparatory pumping processing prior to the start of the steady-state operation is performed, for example, immediately after the start of the gas sensor 100. The preparatory pumping processing will be described in detail below.

In a condition in which the steady-state operation of the gas sensor 100 continues, the sensor element 101 is typically maintained at the element driving temperature, and the pump voltage applied in each pump cell is low, so that an electric field exceeding the first diagnostic threshold is rarely produced between the pump electrodes of each pump cell. The pumping diagnosis may thus be omitted.

<Preparatory Pumping Processing>

As described above, the gas sensor 100 measures the NOx concentration in the steady state of operation. During the steady-state operation, the oxygen partial pressure in the first internal space 20 and the second internal space 40 has a value sufficiently lower than oxygen partial pressure in air.

On the other hand, when the gas sensor 100 stops performing all the operations, naturally no pump cell operates, so that air can enter the gas distribution part through the gas inlet 10 in the sensor element 101. Thus, there is a possibility that the oxygen partial pressure in the first internal space 20 and the second internal space 40 has reached oxygen partial pressure that is at most nearly equal to the oxygen partial pressure in air. The temperature of the sensor element 101 is sufficiently lower than the element driving temperature as the sensor element 101 is not heated by the heater part 70, and might be reduced to about room temperature if the operations are stopped for a long time.

To start the gas sensor 100 in such a stopping state to cause the gas sensor 100 to be in the steady state of operation in which the NOx concentration can successfully be measured, it is necessary to pump out at least a certain amount of oxygen from the first internal space 20 and the second internal space 40 using each pump cell of the sensor element 101 in advance prior to the start. In the present embodiment, such processing to pump out oxygen performed by each pump cell prior to the steady-state operation to achieve a state in which the steady-state operation can be performed is referred to as the preparatory pumping processing.

The preparatory pumping processing is performed through operation of each part under control by the integrated control part 111. To achieve the steady state of operation, it is necessary to heat the sensor element 101 to raise the reduced temperature of the sensor element 101 to the element driving temperature. In many cases, the heating processing also becomes necessary as processing associated with the preparatory pumping processing.

Time required for the gas sensor 100 to be in the steady state of operation from the start thereof, which is also referred to as light-off time, is typically preferably short. Time required for the preparatory pumping processing is thus also basically preferably short. In the preparatory pumping processing, a highest possible voltage exceeding a voltage applied in the steady-state operation is typically applied between the electrodes of each pump cell to pump out a large amount of oxygen in short time.

On the other hand, if such a high voltage is applied when the sensor element 101 is at a high temperature, oxygen might move from the solid electrolyte located between the pair of pump electrodes of each pump cell with production of a strong electric field, to thereby reduce the strength of the sensor element 101 as described above. In the preparatory pumping processing, it is necessary to prevent such movement of oxygen contained in the solid electrolyte.

In the gas sensor 100 according to the present embodiment, the pumping diagnosis is made in the preparatory pumping processing to reduce the light-off time without reducing the strength of the sensor element 101.

Figure 3:
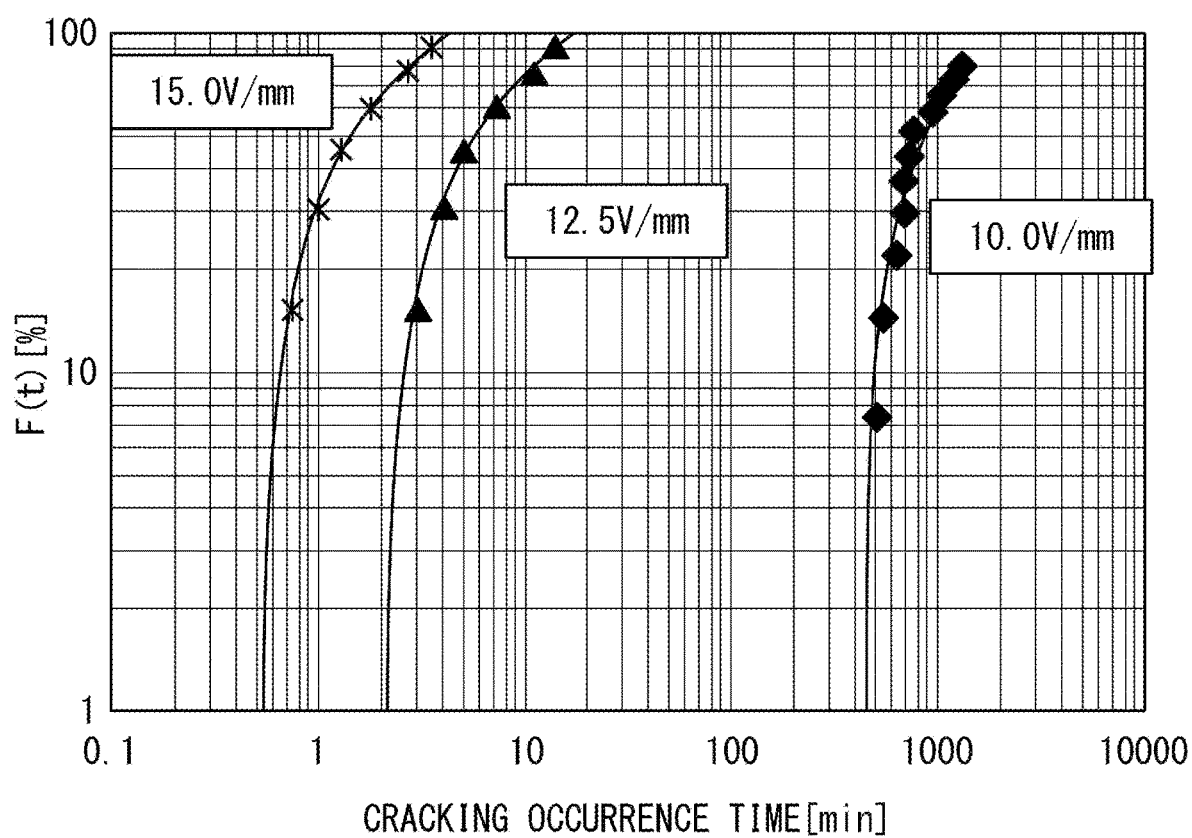
FIG. 3 is a Weibull plot of time (cracking occurrence time) until cracking of a solid electrolyte located between a pair of pump electrodes occurs when a pump voltage is applied to a main pump cell 21 after the temperature of the sensor element 101 is raised from room temperature to 850° C.

FIG. 3 is a Weibull plot of time (cracking occurrence time) from the start of application of the main pump voltage Vp0 until cracking of the solid electrolyte located between the pair of pump electrodes (between the inner pump electrode 22 and the outer pump electrode 23) occurs when the temperature of the sensor element 101 is raised from the room temperature to 850° C. without performing the preparatory pumping processing, and then the pump voltage is applied to the main pump cell 21 for pumping while the temperature is maintained. Specifically, main pump voltages Vp0 having different magnitudes are applied to produce electric fields between the inner pump electrode 22 and the outer pump electrode 23 having three different magnitudes of 10.0 V/mm, 12.5 V/mm, and 15.0 V/mm. A temperature of 850° C. is a temperature that can be set as the element driving temperature.

It is confirmed from FIG. 3 that, the larger the inter-electrode electric field is, the more likely cracking is to occur in short time after application of the pump voltage when the sensor element is in a state of being heated to a high temperature. It is predicted that, in a case where the electric field has a magnitude of 15.0 V/mm, for example, cracking of a few percent of sensor elements 101 has already occurred after the elapse of approximately only 30 seconds (0.5 min) to 40 seconds from the start of application of the main pump voltage Vp0.

In a case of the gas sensor 100 providing the Weibull plot shown in FIG. 3, the first diagnostic threshold for the pumping diagnosis to be applied when the preparatory pumping processing is performed is set to 15.0 V/mm in one preferable example. In this case, time of application of a high voltage between the pair of pump electrodes of each pump cell to produce an electric field having a magnitude greater than 15.0 V/mm can be suppressed to at most 30 seconds even during a temperature rise by the heater part 70. The first diagnostic threshold is more preferably set to 7.5 V/mm.

On the other hand, the second diagnostic threshold is preferably set so that the temperature corresponding to the second diagnostic threshold is 600° C.

The preparatory pumping processing, however, is specifically performed in the gas sensor 100 in two manners differing in setting of the second diagnostic threshold and content of determination based on the setting of the second diagnostic threshold due to a difference in index value (temperature index value) indicating the temperature of the solid electrolyte located between the pump electrodes. These manners will sequentially be described below.

In either case, the pumping operation is started at a high pump voltage that can exceed the first diagnostic threshold, whether the pumping diagnosis can be made is determined based on the second diagnostic threshold, and, in a case where the pumping diagnosis is to be made as a result of determination, the pumping operation is controlled so that the inter-electrode electric field does not exceed the first diagnostic threshold.

In the case that oxygen contained in the solid electrolyte is reduced by continuation of pumping in a state of a high inter-electrode electric field being maintained, the strength of the sensor element 101 containing the solid electrolyte as a main component is reduced to make cracking more likely to occur. It is preferable, in terms of extension of the lifetime of the sensor element 101, to make the pumping diagnosis in the preparatory pumping processing and to reduce the pump voltage in accordance with a result of the pumping diagnosis.

(First Manner)

In the first manner of the preparatory pumping processing, resistivity of the solid electrolyte located between the pump electrodes is used as the temperature index value using the correlation between the temperature of the solid electrolyte located between the pump electrodes and the resistivity of the solid electrolyte, and a value of the resistivity corresponding to 600° C. is set to the second diagnostic threshold.

Resistivity ρ of the solid electrolyte located between the pair of electrodes arranged to oppose each other and being equal in area can typically be expressed by an equation (1) below, where R is a resistance value, d is an inter-electrode distance between the electrodes, and S is an electrode area as the area of each of the electrodes.

$$\rho = R \cdot S / d \quad (1)$$

In the present embodiment, however, although the resistance value R can be calculated by dividing the pump voltage by the pump current, a pair of electrodes of each of the main pump cell 21, the auxiliary pump cell 50, and the measurement pump cell 41 included in the sensor element 101 is not necessarily equal in area, and the pair of electrodes of each pump cell is not necessarily arranged to oppose each other. For ease of calculation, the resistivity ρ is calculated using the equation (1) after the inter-electrode distance d and the electrode area S of each pump cell are defined to be simplified as described below.

Strictly speaking, each calculated value thus does not necessarily represent the resistivity between the electrodes of each pump cell, and is nothing more than a relative evaluation value (a resistivity evaluation value) indicating a relative magnitude of the resistivity. At least in the preparatory pumping processing, however, use of the calculated value as the value indicating the resistivity between the electrodes of each pump cell does not cause any problems as it is unnecessary to compare the resistivity between different pump cells.

First, as for the main pump cell 21, the thickness of the second solid electrolyte layer 6 located between the ceiling electrode portion 22a of the inner pump electrode 22 and the outer pump electrode 23 is set to the inter-electrode distance d, and a smaller one of the area of the ceiling electrode portion 22a and the area of the outer pump electrode 23 is set to the electrode area S.

Similarly as for the auxiliary pump cell 50, the thickness of the second solid electrolyte layer 6 located between the ceiling electrode portion 51a of the auxiliary pump electrode 51 and the outer pump electrode 23 is set to the inter-electrode distance d, and a smaller one of the area of the ceiling electrode portion 51a and the area of the outer pump electrode 23 is set to the electrode area S.

On the other hand, as for the measurement pump cell 41, the sum of the thickness of the spacer layer 5 and the thickness of the second solid electrolyte layer 6 is set to the inter-electrode distance d, and a smaller one of the area of the measurement electrode 44 and the area of the outer pump electrode 23 is set to the electrode area S.

The inter-electrode distance d and the electrode area S are (known) values that can be identified in advance in the sensor element 101, and thus, in a case where they are identified, a change in temperature of the solid electrolyte between the pump electrodes can practically be grasped in the preparatory pumping processing performed in this manner by grasping the pump voltage and the pump current in each pump cell.

Figure 4:
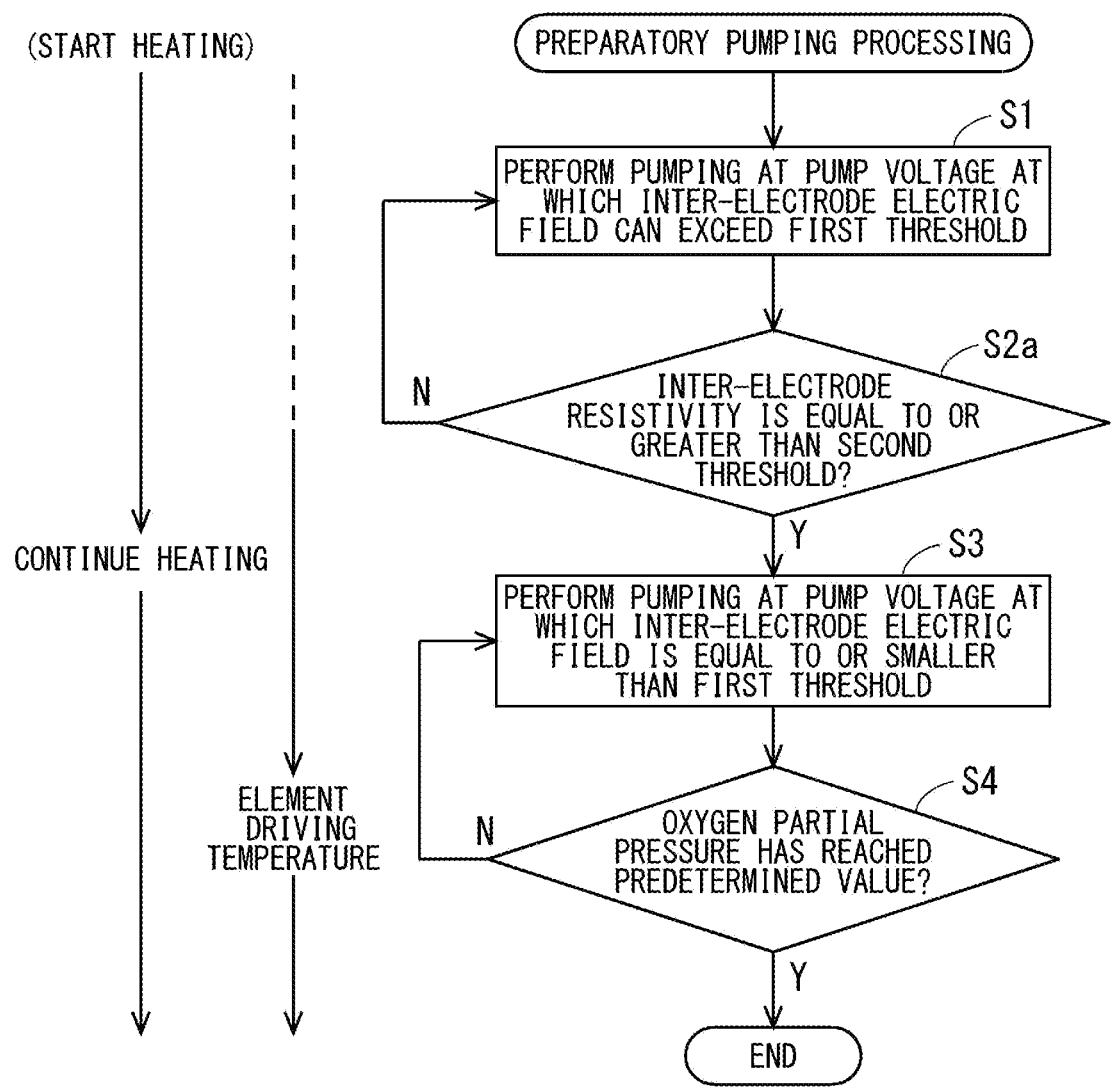
FIG. 4 is a diagram showing a process flow in a first manner of preparatory pumping processing.

FIG. 4 is a diagram showing a process flow in the first manner of the preparatory pumping processing. A heating condition and a temperature condition of the sensor element 101 during the preparatory pumping processing are also shown in FIG. 4.

In a case where the temperature of the sensor element 101 is lower than the element driving temperature on the occasion of the preparatory pumping processing, such as a case where the gas sensor 100 is not started, the heater part 70 starts heating the sensor element 101 in execution of the preparatory pumping processing. The heater part 70 continues heating even after the sensor element 101 has reached the element driving temperature. Alternatively, the preparatory pumping processing is performed while the heater part 70 continues heating in some cases. In other words, the preparatory pumping processing is performed in a condition in which the heater part 70 performs heating to raise the temperature or maintain the temperature at the element driving temperature.

Description will be made below by taking, as an example, a case where the temperature of the sensor element 101 is lower than the element driving temperature at the start of the preparatory pumping processing.

In this case, after the heater part 70 starts heating to start a temperature rise of the sensor element 101 under control instructions from the integrated control part 111, the main pump control part 112, the auxiliary pump control part 113, and the measurement pump control part 114 respectively control the variable power supply 24, the variable power supply 52, and the variable power supply 46 to start pumping to pump out oxygen in air having entered the gas distribution part (mainly the first internal space 20 and the second internal space 40) by the main pump cell 21, the auxiliary pump cell 50, and the measurement pump cell 41 (step S1). At the same time, the pumping diagnostic part 117 starts determining whether inter-electrode resistivity is equal to or greater than the second diagnostic threshold (SECOND THRESHOLD in FIG. 4) (step S2a).

A highest possible pump voltage is preferably applied in each pump cell at pumping in terms of early pumping of oxygen. Thus, while the temperature of the sensor element 101 is relatively low after the start of heating until the inter-electrode resistivity reaches the second diagnostic threshold (NO in step S2a), the pump voltage is allowed to exceed not only a value of the voltage in the steady-state operation but also the first diagnostic threshold (FIRST THRESHOLD in FIG. 4).

The pump voltage is approximately at most 2.5 V in actuality although it varies depending on the pump cell. The pump voltage, however, is not required to be constant.

When the temperature of the solid electrolyte between the pump electrodes increases as the heater part 70 continues heating, the inter-electrode resistivity increases with the increase in temperature of the solid electrolyte, and the pumping diagnostic part 117 determines that the inter-electrode resistivity has increased to be equal to or greater than the second diagnostic threshold (YES in step S2a), the pump voltage is reduced under control instructions from the integrated control part 111 (step S3). The pump voltage is reduced by the pumping diagnostic part 117 until the pumping diagnostic part 117 determines that the inter-electrode electric field is greater.

A manner in which the temperature of the solid electrolyte between the pump electrodes increases, the pumping condition, and the like vary among individual pump cells, so that the pumping diagnostic part 117 may make the diagnosis in step S2a and reduce the pump voltage after the diagnosis separately for each of the pump cells. That is to say, the pumping diagnosis during the preparatory pumping processing may be made for each of the pump cells independently of one another. In other words, the process flow shown in FIG. 4 is applicable to individual pump cells. That is to say, even if the inter-electrode resistivity is equal to or greater than the second diagnostic threshold in any of the pump cells, the inter-electrode resistivity may sometimes be smaller than the second diagnostic threshold in the other pump cells. This means that a result of a diagnosis for a certain pump cell does not affect the other pump cells.

Thus, even if a pumping voltage is reduced in a certain pump cell as the inter-electrode resistivity has reached the second diagnostic threshold unique to the certain pump cell, an original pumping manner from the start may be maintained in another pump cell in a case where the inter-electrode resistivity has not reached the second diagnostic threshold set for that pump cell.

Even after the pumping voltage is reduced, pumping operation itself at the pump voltage continues (NO in step S4) until oxygen partial pressure in a pumping target region (the first internal space 20, the second internal space 40, and a region near the surface of the measurement electrode 44 covered with the fourth diffusion control part 45) reaches a predetermined value substantially allowing for the steady-state operation (YES in step S4).

The temperature of the sensor element 101 typically reaches the element driving temperature after the inter-electrode resistivity becomes equal to or greater than the second diagnostic threshold until the oxygen partial pressure in the pumping target region is reduced to substantially allow for the steady-state operation, and thus the steady-state operation can be performed in the gas sensor 100 by achieving a state in which the oxygen partial pressure is sufficiently reduced.

(Second Manner)

In the second manner of the preparatory pumping processing, by using the fact that the temperature of the solid electrolyte located between the pump electrodes changes in accordance with heating performed by the heater part 70 (more specifically, in accordance with heat generation of the heater element 72), the relationship therebetween is experimentally identified in advance, and then, the heating temperature of the heater part 70 (heater temperature) is directly adopted as the temperature index value indicating the temperature of the solid electrolyte located between the pump electrodes, and a value of the heating temperature corresponding to 600° C. is set to the second diagnostic threshold.

Figure 5:
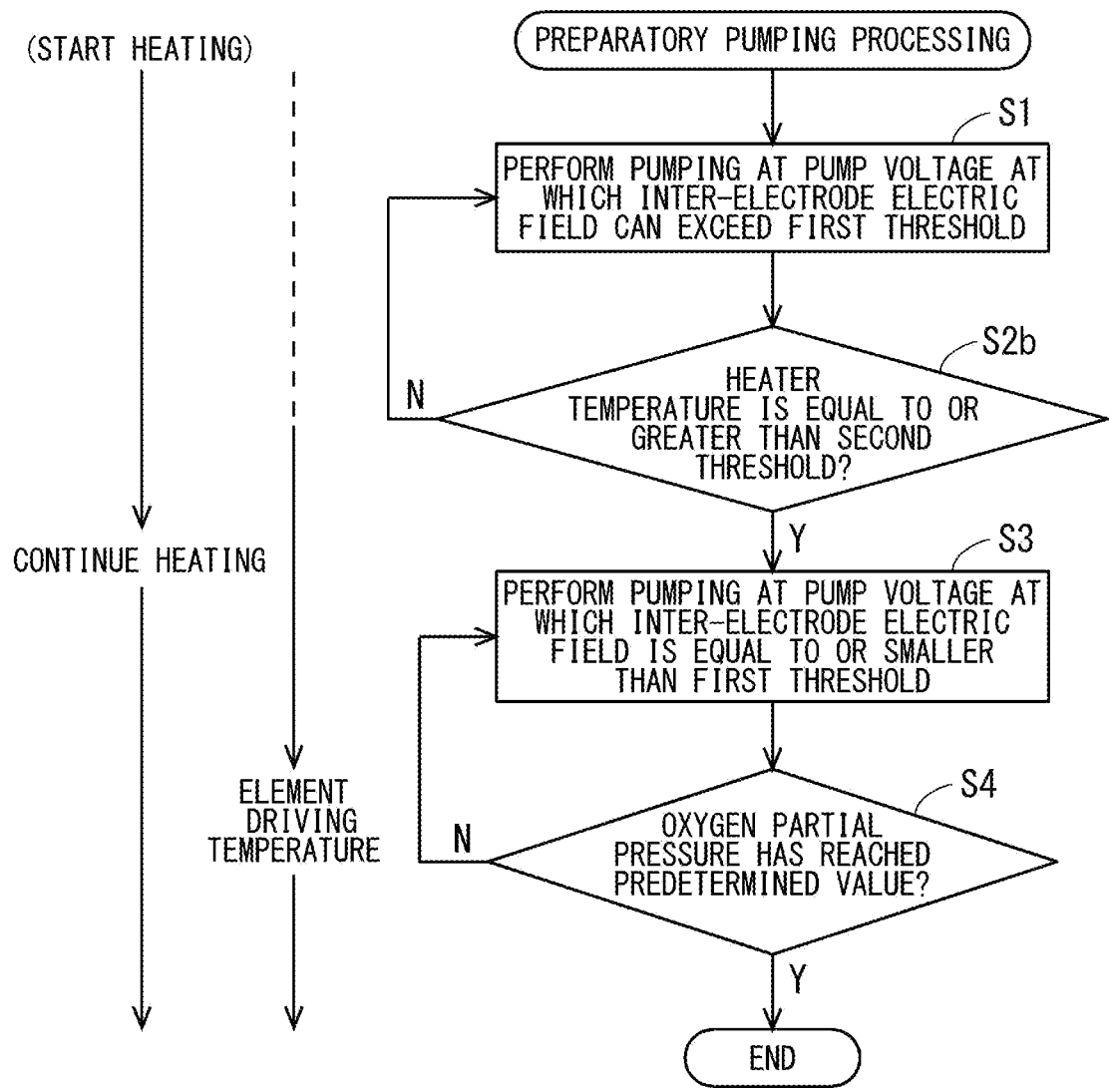
FIG. 5 is a diagram showing a process flow in a second manner of the preparatory pumping processing.

FIG. 5 is a diagram showing a process flow in the second manner of the preparatory pumping processing. The heating condition and the temperature condition of the sensor element 101 during the preparatory pumping processing are also shown in FIG. 5.

The process flow shown in FIG. 5 is the same as the process flow in the first manner shown in FIG. 4 except that step S2a is replaced by step S2b. In the second manner, after the start of pumping based on the control instructions from the integrated control part 111 (step S1), the pumping diagnostic part 117 starts determining whether the heating temperature of the heater part 70 is equal to or greater than the second diagnostic threshold (SECOND THRESHOLD in FIG. 5) (step S2b). While the temperature of the sensor element 101 is relatively low after the start of heating until the heater temperature reaches the second diagnostic threshold (NO in step S2b), the pump voltage is allowed to exceed the first diagnostic threshold. When the heater temperature then increases as the heater part 70 continues heating, and the pumping diagnostic part 117 determines that the heater temperature has increased to be equal to or greater than the second diagnostic threshold (YES in step S2b), the pump voltage is reduced under control performed by the integrated control part 111 (step S3). Processing thereafter is the same as that in the first manner. The process flow shown in FIG. 5 is also applicable to individual pump cells.

The heater temperature is identified based on the heater resistance as the resistance value of the heater resistance detection lead 75 included in the heater part 70, so that the heater resistance itself may be used as the temperature index value, and the second diagnostic threshold may be set for the heater resistance.

As described above, according to the present embodiment, when oxygen existing in the internal space of the sensor element is pumped out by the pump cell to cause the oxygen partial pressure in the internal space to have a predetermined value, for example, when the gas sensor in an operation-stopped state is put into a state in which the steady-state operation can be performed to measure the concentration, a high voltage is applied while the temperature of the solid electrolyte located between the pump electrodes is low, and the voltage applied to the pump cell is suppressed to a voltage not causing movement of oxygen from the solid electrolyte once the temperature of the solid electrolyte becomes equal to or greater than a predetermined threshold. Pumping out of oxygen from the internal space and the like can thus be completed early without causing cracking of the solid electrolyte located between the pump electrodes. The lifetime of the sensor element and further the lifetime of the gas sensor can thereby be extended.

<Modification>

In the above-mentioned embodiment, the measurement electrode 44 is disposed in the second internal space 40 to be covered with the fourth diffusion control part 45 functioning as the porous protective film and providing the predetermined diffusion resistance to the measurement gas, and the amount of NOx flowing into the measurement electrode 44 is limited by the fourth diffusion control part 45. Alternatively, however, a third internal space communicating with the second internal space 40, for example, through a slit-like or porous diffusion control part providing, to the measurement gas, diffusion resistance equivalent to the diffusion resistance provided by the fourth diffusion control part 45 may be provided, and the measurement electrode 44 may be provided in the third internal space.

Figure 6:
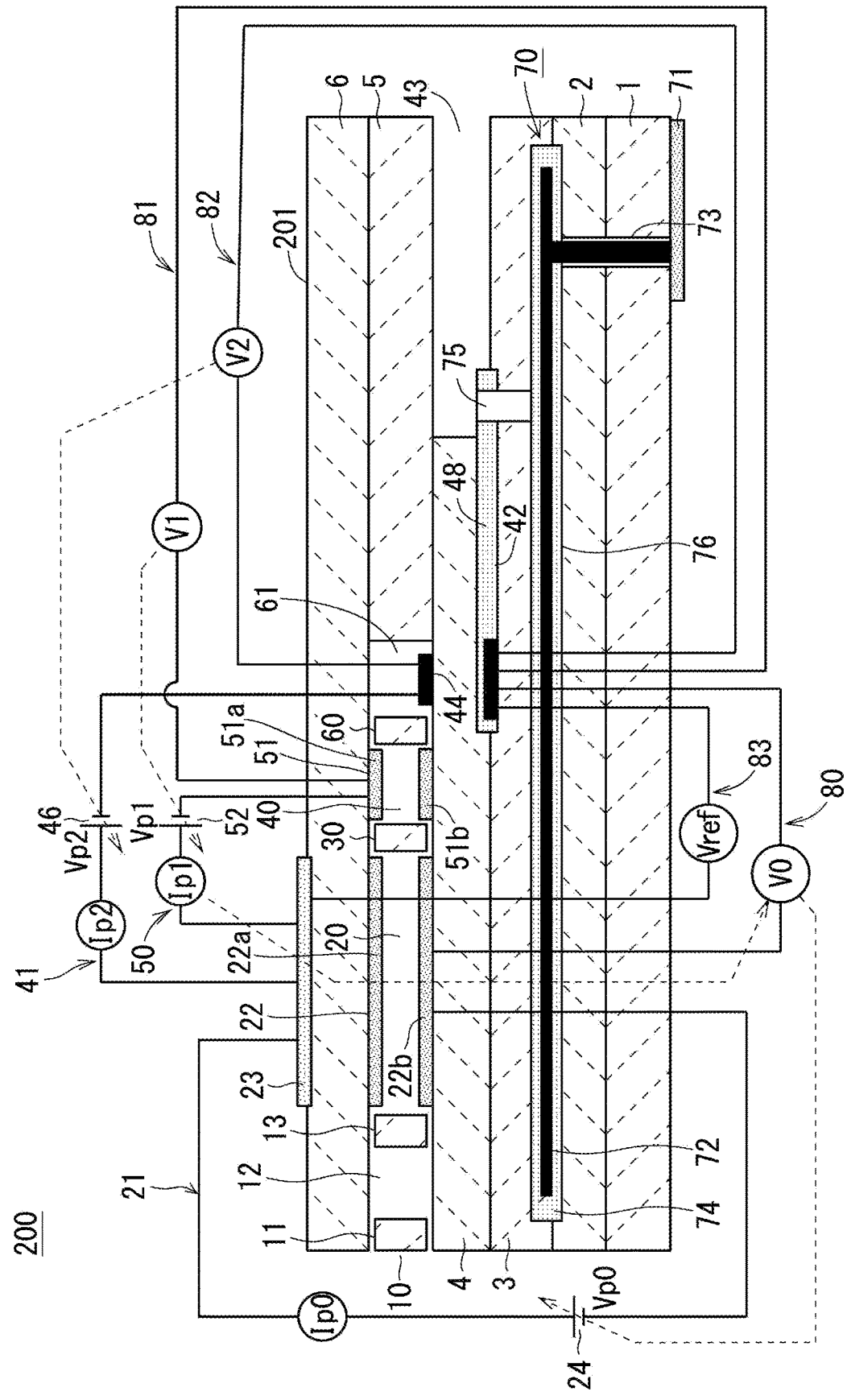
FIG. 6 is a diagram schematically showing one example of a configuration of a gas sensor 200, including a vertical cross-sectional view taken along a longitudinal direction of a sensor element 201.

FIG. 6 is a diagram schematically showing one example of a configuration of a gas sensor 200, including a vertical sectional view taken along a longitudinal direction of a sensor element 201 having such a configuration. The sensor element 201 includes components having action and functions in common with the components of the sensor element 101 illustrated in FIG. 1. Such components bear the same reference signs as those of the corresponding components illustrated in FIG. 1, and detailed description thereof is omitted unless it is necessary. The controller 110 is not illustrated.

The sensor element 201 is different from the sensor element 101 illustrated in FIG. 1 in that the first diffusion control part 11 doubles as the gas inlet 10, a third internal space 61 communicating with the second internal space 40 through a slit-like fifth diffusion control part 60 similar to the first diffusion control part 11, the second diffusion control part 13, and the third diffusion control part 30 is provided, the measurement electrode 44 is provided on an upper surface of a portion of the first solid electrolyte layer 4 facing the third internal space 61, and the measurement electrode 44 is exposed to the third internal space 61. The sensor element 201, however, is similar to the sensor element 101 in that a diffusion control part is located between the second internal space 40 and the measurement electrode 44.

The gas sensor 200 is different from the gas sensor 100 in the above-mentioned embodiment in that the measurement pump cell 41 is to pump out oxygen having entered the third internal space in the preparatory pumping processing. In the other respects, the gas sensor 200 can perform the preparatory pumping processing in a similar manner to the gas sensor 100.

Since the pumping diagnosis is processing to determine whether an excessively large inter-electrode electric field acts on the solid electrolyte as described above, a time of the pumping diagnosis not limited to a time during the preparatory pumping processing.

For example, in a case where the sensor element includes an electrode to decompose NOx, such as the measurement electrode 44, and the electrode contains rhodium (Rh), processing to apply a large voltage to a pump cell to decompose moisture in the measurement gas is sometimes performed for the purpose of preventing oxidation of Rh contained in the electrode. In such a case, the pumping diagnosis can be made to reduce the pump voltage in a case where an excessively large inter-electrode electric field is produced.

While the invention has been shown and described in detail, the foregoing description is in all aspects illustrative and not restrictive. It is therefore understood that numerous modifications and variations can be devised without departing from the scope of the invention.

What is claimed is:

1. A limiting-current type gas sensor measuring concentration of NOx in a measurement gas, said gas sensor comprising:
   a sensor element including:
      a base part made of an oxygen-ion conductive solid electrolyte;
      at least one pump cell as an electrochemical pump cell including:
         a first electrode disposed to be capable of being in contact with said measurement gas introduced into said sensor element; and
         a second electrode disposed so that a part made of said solid electrolyte is located between said first electrode and said second electrode,
      and said at least one pump cell capable of externally pumping out oxygen from a region that said first electrode faces through application of a predetermined pump voltage between said first electrode and said second electrode; and
      a heater part buried in said sensor element and heating said sensor element; and
   a controller controlling operation of said gas sensor, said controller being configured to:
      apply said predetermined pump voltage between said first electrode and said second electrode,
      determine an inter-electrode electric field produced in said part made of said solid electrolyte between said first electrode and said second electrode through the application of said predetermined pump voltage between said first electrode and said second electrode, and
      determine whether the inter-electrode electric field exceeds a first threshold, wherein
   upon a temperature of the sensor element being lower than an element driving temperature at a start of the gas sensor, the controller controls said heater part to raise the temperature of said sensor element to said element driving temperature and applies said predetermined pump voltage between said first electrode and said second electrode, and upon determining said inter-electrode electric field exceeds said first threshold, the controller is configured to reduce said predetermined pump voltage so that said inter-electrode electric field falls below said first threshold.

2. The gas sensor according to claim 1, wherein the controller is configured to determine whether a temperature index value exceeds a second threshold, said temperature index value having a positive correlation with temperature in said part made of said solid electrolyte between said first electrode and said second electrode, and the controller is configured to determine whether the inter-electrode electric field exceeds said first threshold when said temperature index value is equal to or greater than said second threshold.

3. The gas sensor according to claim 2, wherein
said temperature index value is resistivity in said part made of said solid electrolyte between said first electrode and said second electrode.

4. The gas sensor according to claim 3, wherein
said concentration of NOx in said measurement gas is measured in a steady state of operation, said steady state of operation being a state in which said sensor element is maintained at said element driving temperature by being heated by said heater part, and oxygen partial pressure in said region that said first electrode faces in said at least one pump cell is maintained at or below a predetermined value, said at least one pump cell performs preparatory pumping to pump out oxygen from said region while said heater part raises temperature of said sensor element to said element driving temperature, so that said gas sensor transitions from a non-steady state of operation to said steady state of operation, and the controller determines whether said inter-electrode electric field exceeds said first threshold and determines whether said temperature index value exceeds said second threshold during transition from said non-steady state of operation to said steady state of operation.

5. The gas sensor according to claim 4, wherein
said sensor element further includes:
a gas inlet through which said measurement gas is introduced from an external space;
a first internal space communicating with said gas inlet under predetermined diffusion resistance;
a main pump cell as one of said at least one pump cell, said main pump cell including an inner pump electrode as one of said first electrode located to face said first internal space, an out-of-space pump electrode as said second electrode located to face a space other than said first internal space, and said solid electrolyte between said inner pump electrode and said out-of-space pump electrode as one of said part made of said solid electrolyte between said first electrode and said second electrode;
a second internal space communicating with said first internal space under predetermined diffusion resistance;
an auxiliary pump cell as another one of said at least one pump cell, said auxiliary pump cell including an auxiliary pump electrode as another one of said first electrode located to face said second internal space, said out-of-space pump electrode, and said solid electrolyte between said auxiliary pump electrode and said out-of-space pump electrode as another one of said part made of said solid electrolyte between said first electrode and said second electrode;
a measurement electrode as yet another one of said first electrode located inside said sensor element, at least one diffusion control part being located between said measurement electrode and said second internal space;
a measurement pump cell as yet another one of said at least one pump cell, said measurement pump cell including said measurement electrode, said out-of-space pump electrode, and said solid electrolyte located between said measurement electrode and said out-of-space pump electrode; and
a reference electrode located inside said sensor element and capable of being in contact with a reference gas, said gas sensor further includes:
a first variable power supply to apply a main pump voltage between said out-of-space pump electrode and said inner pump electrode;
a second variable power supply to apply an auxiliary pump voltage between said out-of-space pump electrode and said auxiliary pump electrode; and
a third variable power supply to apply a measurement pump voltage between said out-of-space pump electrode and said measurement electrode, in said steady state of operation,
said first variable power supply applies said main pump voltage so that an oxygen concentration in said first internal space is constant,
said second variable power supply applies said auxiliary pump voltage so that an oxygen concentration in said second internal space is constant, and
said third variable power supply applies said measurement pump voltage so that oxygen generated through decomposition of NOx in said measurement electrode is pumped out.

6. The gas sensor according to claim 2, wherein
said temperature index value is a heater temperature identified from a resistance value of a heating element included in said heater part, or is said resistance value itself.

7. The gas sensor according to claim 6, wherein
said concentration of NOx in said measurement gas is measured in a steady state of operation, said steady state of operation being a state in which said sensor element is maintained at said element driving temperature by being heated by said heater part, and oxygen partial pressure in said region that said first electrode faces in said at least one pump cell is maintained at or below a predetermined value, said at least one pump cell performs preparatory pumping to pump out oxygen from said region while said heater part raises temperature of said sensor element to said element driving temperature, so that said gas sensor transitions from a non-steady state of operation to said steady state of operation, and the controller determines whether said inter-electrode electric field exceeds said first threshold and determines whether said temperature index value exceeds said second threshold during transition from said non-steady state of operation to said steady state of operation.

8. The gas sensor according to claim 7, wherein
said sensor element further includes:
a gas inlet through which said measurement gas is introduced from an external space;
a first internal space communicating with said gas inlet under predetermined diffusion resistance;
a main pump cell as one of said at least one pump cell, said main pump cell including an inner pump electrode as one of said first electrode located to face said first internal space, an out-of-space pump electrode as said second electrode located to face a space other than said first internal space, and said solid electrolyte between said inner pump electrode and said out-of-space pump electrode as one of said part made of said solid electrolyte between said first electrode and said second electrode;

a second internal space communicating with said first internal space under predetermined diffusion resistance;

an auxiliary pump cell as another one of said at least one pump cell, said auxiliary pump cell including an auxiliary pump electrode as another one of said first electrode located to face said second internal space, said out-of-space pump electrode, and said solid electrolyte between said auxiliary pump electrode and said out-of-space pump electrode as another one of said part made of said solid electrolyte between said first electrode and said second electrode;

a measurement electrode as yet another one of said first electrode located inside said sensor element, at least one diffusion control part being located between said measurement electrode and said second internal space;

a measurement pump cell as yet another one of said at least one pump cell, said measurement pump cell including said measurement electrode, said out-of-space pump electrode, and said solid electrolyte located between said measurement electrode and said out-of-space pump electrode; and a reference electrode located inside said sensor element and capable of being in contact with a reference gas, said gas sensor further includes:
 a first variable power supply to apply a main pump voltage between said out-of-space pump electrode and said inner pump electrode;
 a second variable power supply to apply an auxiliary pump voltage between said out-of-space pump electrode and said auxiliary pump electrode; and
 a third variable power supply to apply a measurement pump voltage between said out-of-space pump electrode and said measurement electrode, in said steady state of operation,
 said first variable power supply applies said main pump voltage so that an oxygen concentration in said first internal space is constant,
 said second variable power supply applies said auxiliary pump voltage so that an oxygen concentration in said second internal space is constant, and
 said third variable power supply applies said measurement pump voltage so that oxygen generated through decomposition of NOx in said measurement electrode is pumped out.

9. The gas sensor according to claim 2, wherein
said concentration of NOx in said measurement gas is measured in a steady state of operation, said steady state of operation being a state in which said sensor element is maintained at said element driving temperature by being heated by said heater part, and oxygen partial pressure in said region that said first electrode faces in said at least one pump cell is maintained at or below a predetermined value,
said at least one pump cell performs preparatory pumping to pump out oxygen from said region while said heater part raises temperature of said sensor element to said element driving temperature, so that said gas sensor transitions from a non-steady state of operation to said steady state of operation, and
the controller determines whether said inter-electrode electric field exceeds said first threshold and determines whether said temperature index value exceeds said second threshold during transition from said non-steady state of operation to said steady state of operation.

10. The gas sensor according to claim 9, wherein
said sensor element further includes:
 a gas inlet through which said measurement gas is introduced from an external space;
 a first internal space communicating with said gas inlet under predetermined diffusion resistance;
 a main pump cell as one of said at least one pump cell, said main pump cell including an inner pump electrode as one of said first electrode located to face said first internal space, an out-of-space pump electrode as said second electrode located to face a space other than said first internal space, and said solid electrolyte between said inner pump electrode and said out-of-space pump electrode as one of said part made of said solid electrolyte between said first electrode and said second electrode;
 a second internal space communicating with said first internal space under predetermined diffusion resistance;
 an auxiliary pump cell as another one of said at least one pump cell, said auxiliary pump cell including an auxiliary pump electrode as another one of said first electrode located to face said second internal space, said out-of-space pump electrode, and said solid electrolyte between said auxiliary pump electrode and said out-of-space pump electrode as another one of said part made of said solid electrolyte between said first electrode and said second electrode;
 a measurement electrode as yet another one of said first electrode located inside said sensor element, at least one diffusion control part being located between said measurement electrode and said second internal space;
 a measurement pump cell as yet another one of said at least one pump cell, said measurement pump cell including said measurement electrode, said out-of-space pump electrode, and said solid electrolyte located between said measurement electrode and said out-of-space pump electrode; and
 a reference electrode located inside said sensor element and capable of being in contact with a reference gas,
said gas sensor further includes:
 a first variable power supply to apply a main pump voltage between said out-of-space pump electrode and said inner pump electrode;
 a second variable power supply to apply an auxiliary pump voltage between said out-of-space pump electrode and said auxiliary pump electrode; and
 a third variable power supply to apply a measurement pump voltage between said out-of-space pump electrode and said measurement electrode,
in said steady state of operation,
 said first variable power supply applies said main pump voltage so that an oxygen concentration in said first internal space is constant,
 said second variable power supply applies said auxiliary pump voltage so that an oxygen concentration in said second internal space is constant, and
 said third variable power supply applies said measurement pump voltage so that oxygen generated through decomposition of NOx in said measurement electrode is pumped out.

11. A method for controlling operation of a limiting-current type gas sensor measuring concentration of NOx in a measurement gas, wherein
said gas sensor includes a sensor element including:
a base part made of an oxygen-ion conductive solid electrolyte;
at least one pump cell as an electrochemical pump cell including:
a first electrode disposed to be capable of being in contact with said measurement gas introduced into said sensor element; and
a second electrode disposed so that a part made of said solid electrolyte is located between said first electrode and said second electrode,
and said at least one pump cell being capable of externally pumping out oxygen from a region that said first electrode faces through application of a predetermined pump voltage between said first electrode and said second electrode; and
a heater part buried in said sensor element and heating said sensor element,
said method including:
a) applying said predetermined pump voltage between said first electrode and said second electrode; and
b) making a first diagnosis to determine whether an inter-electrode electric field produced in said part made of said solid electrolyte between said first electrode and said second electrode through application of said predetermined pump voltage between said first electrode and said second electrode in said step a) exceeds a first threshold, wherein
upon a temperature of the sensor element being lower than an element driving temperature at a start of the gas sensor, controlling said heater part to raise the temperature of said sensor element to said element driving temperature and applying said predetermined pump voltage between said first electrode and said second electrode, and upon determining said inter-electrode electric field exceeds said first threshold in said step b), said predetermined pump voltage applied in said step a) is reduced so that said inter-electrode electric field falls below said first threshold.

12. The method for controlling operation of said gas sensor according to claim 11, wherein
a second diagnosis is further made in said step b), said second diagnosis determining whether a temperature index value exceeds a second threshold, said temperature index value having a positive correlation with temperature in said part made of said solid electrolyte between said first electrode and said second electrode, and
said first diagnosis is made when said temperature index value is equal to or greater than said second threshold.

13. The method for controlling operation of said gas sensor according to claim 12, wherein
said temperature index value is resistivity in said part made of said solid electrolyte between said first electrode and said second electrode.

14. The method for controlling operation of said gas sensor according to claim 13, wherein
said concentration of NOx in said measurement gas is measured by said gas sensor in a steady state of operation, said steady state of operation being a state in which said sensor element is maintained at said element driving temperature by being heated by said heater part, and oxygen partial pressure in said region that said first electrode faces in said at least one pump cell is maintained at or below a predetermined value,
said method further includes
c) causing said gas sensor to transition from a non-steady state of operation to said steady state of operation, said step c) including:
c-1) raising temperature of said sensor element to said element driving temperature using said heater part; and
c-2) pumping out oxygen from said region using said at least one pump cell during said step c-1), and
said first diagnosis and said second diagnosis in said step b) are made during said step c).

15. The method for controlling operation of said gas sensor according to claim 14, wherein
said sensor element further includes:
a gas inlet through which said measurement gas is introduced from an external space;
a first internal space communicating with said gas inlet under predetermined diffusion resistance;
a main pump cell as one of said at least one pump cell, said main pump cell including an inner pump electrode as one of said first electrode located to face said first internal space, an out-of-space pump electrode as said second electrode located to face a space other than said first internal space, and said solid electrolyte between said inner pump electrode and said out-of-space pump electrode as one of said part made of said solid electrolyte between said first electrode and said second electrode;
a second internal space communicating with said first internal space under predetermined diffusion resistance;
an auxiliary pump cell as another one of said at least one pump cell, said auxiliary pump cell including an auxiliary pump electrode as another one of said first electrode located to face said second internal space, said out-of-space pump electrode, and said solid electrolyte between said auxiliary pump electrode and said out-of-space pump electrode as another one of said part made of said solid electrolyte between said first electrode and said second electrode;
a measurement electrode as yet another one of said first electrode located inside said sensor element, at least one diffusion control part being located between said measurement electrode and said second internal space;
a measurement pump cell as yet another one of said at least one pump cell, said measurement pump cell including said measurement electrode, said out-of-space pump electrode, and said solid electrolyte located between said measurement electrode and said out-of-space pump electrode; and
a reference electrode located inside said sensor element and capable of being in contact with a reference gas,
said gas sensor further includes:
a first variable power supply to apply a main pump voltage between said out-of-space pump electrode and said inner pump electrode;
a second variable power supply to apply an auxiliary pump voltage between said out-of-space pump electrode and said auxiliary pump electrode; and
a third variable power supply to apply a measurement pump voltage between said out-of-space pump electrode and said measurement electrode,
in said steady state of operation, said first variable power supply applies said main pump voltage so that an oxygen concentration in said first internal space is constant, said second variable power supply applies said auxiliary pump voltage so that an oxygen concentration in said second internal space is constant, and said third variable power supply applies said measurement pump voltage so that oxygen generated through decomposition of NOx in said measurement electrode is pumped out.

16. The method for controlling operation of said gas sensor according to claim 12, wherein said temperature index value is a heater temperature identified from a resistance value of a heating element included in said heater part, or is said resistance value itself.

17. The method for controlling operation of said gas sensor according to claim 16, wherein said concentration of NOx in said measurement gas is measured by said gas sensor in a steady state of operation, said steady state of operation being a state in which said sensor element is maintained at said element driving temperature by being heated by said heater part, and oxygen partial pressure in said region that said first electrode faces in said at least one pump cell is maintained at or below a predetermined value, said method further includes c) causing said gas sensor to transition from a non-steady state of operation to said steady state of operation, said step c) including:
  c-1) raising temperature of said sensor element to said element driving temperature using said heater part; and
  c-2) pumping out oxygen from said region using said at least one pump cell during said step c-1), and
said first diagnosis and said second diagnosis in said step b) are made during said step c).

18. The method for controlling operation of said gas sensor according to claim 17, wherein said sensor element further includes:
  a gas inlet through which said measurement gas is introduced from an external space;
  a first internal space communicating with said gas inlet under predetermined diffusion resistance;
  a main pump cell as one of said at least one pump cell, said main pump cell including an inner pump electrode as one of said first electrode located to face said first internal space, an out-of-space pump electrode as said second electrode located to face a space other than said first internal space, and said solid electrolyte between said inner pump electrode and said out-of-space pump electrode as one of said part made of said solid electrolyte between said first electrode and said second electrode;
  a second internal space communicating with said first internal space under predetermined diffusion resistance;
  an auxiliary pump cell as another one of said at least one pump cell, said auxiliary pump cell including an auxiliary pump electrode as another one of said first electrode located to face said second internal space, said out-of-space pump electrode, and said solid electrolyte between said auxiliary pump electrode and said out-of-space pump electrode as another one of said part made of said solid electrolyte between said first electrode and said second electrode;
  a measurement electrode as yet another one of said first electrode located inside said sensor element, at least one diffusion control part being located between said measurement electrode and said second internal space;
  a measurement pump cell as yet another one of said at least one pump cell, said measurement pump cell including said measurement electrode, said out-of-space pump electrode, and said solid electrolyte located between said measurement electrode and said out-of-space pump electrode; and
  a reference electrode located inside said sensor element and capable of being in contact with a reference gas, said gas sensor further includes:
  a first variable power supply to apply a main pump voltage between said out-of-space pump electrode and said inner pump electrode;
  a second variable power supply to apply an auxiliary pump voltage between said out-of-space pump electrode and said auxiliary pump electrode; and
  a third variable power supply to apply a measurement pump voltage between said out-of-space pump electrode and said measurement electrode, in said steady state of operation,
  said first variable power supply applies said main pump voltage so that an oxygen concentration in said first internal space is constant,
  said second variable power supply applies said auxiliary pump voltage so that an oxygen concentration in said second internal space is constant, and
  said third variable power supply applies said measurement pump voltage so that oxygen generated through decomposition of NOx in said measurement electrode is pumped out.

19. The method for controlling operation of said gas sensor according to claim 12, wherein said concentration of NOx in said measurement gas is measured by said gas sensor in a steady state of operation, said steady state of operation being a state in which said sensor element is maintained at said element driving temperature by being heated by said heater part, and oxygen partial pressure in said region that said first electrode faces in said at least one pump cell is maintained at or below a predetermined value, said method further includes
  c) causing said gas sensor to transition from a non-steady state of operation to said steady state of operation, said step c) including:
    c-1) raising temperature of said sensor element to said element driving temperature using said heater part; and
    c-2) pumping out oxygen from said region using said at least one pump cell during said step c-1), and
  said first diagnosis and said second diagnosis in said step b) are made during said step c).

20. The method for controlling operation of said gas sensor according to claim 19, wherein said sensor element further includes:
  a gas inlet through which said measurement gas is introduced from an external space;
  a first internal space communicating with said gas inlet under predetermined diffusion resistance;
  a main pump cell as one of said at least one pump cell, said main pump cell including an inner pump electrode as one of said first electrode located to face said first internal space, an out-of-space pump electrode as said second electrode located to face a space other than said first internal space, and said solid electrolyte between said inner pump electrode and said out-of-space pump electrode as one of said part made of said solid electrolyte between said first electrode and said second electrode;

a second internal space communicating with said first internal space under predetermined diffusion resistance;

an auxiliary pump cell as another one of said at least one pump cell, said auxiliary pump cell including an auxiliary pump electrode as another one of said first electrode located to face said second internal space, said out-of-space pump electrode, and said solid electrolyte between said auxiliary pump electrode and said out-of-space pump electrode as another one of said part made of said solid electrolyte between said first electrode and said second electrode;

a measurement electrode as yet another one of said first electrode located inside said sensor element, at least one diffusion control part being located between said measurement electrode and said second internal space;

a measurement pump cell as yet another one of said at least one pump cell, said measurement pump cell including said measurement electrode, said out-of-space pump electrode, and said solid electrolyte located between said measurement electrode and said out-of-space pump electrode; and a reference electrode located inside said sensor element and capable of being in contact with a reference gas, said gas sensor further includes:

a first variable power supply to apply a main pump voltage between said out-of-space pump electrode and said inner pump electrode;

a second variable power supply to apply an auxiliary pump voltage between said out-of-space pump electrode and said auxiliary pump electrode; and a third variable power supply to apply a measurement pump voltage between said out-of-space pump electrode and said measurement electrode, in said steady state of operation, said first variable power supply applies said main pump voltage so that an oxygen concentration in said first internal space is constant, said second variable power supply applies said auxiliary pump voltage so that an oxygen concentration in said second internal space is constant, and said third variable power supply applies said measurement pump voltage so that oxygen generated through decomposition of NOx in said measurement electrode is pumped out.

* * * * *